(12) United States Patent
Mo et al.

(10) Patent No.: US 6,296,612 B1
(45) Date of Patent: Oct. 2, 2001

(54) METHOD AND APPARATUS FOR ADAPTIVE WALL FILTERING IN SPECTRAL DOPPLER ULTRASOUND IMAGING

(75) Inventors: Larry Y. L. Mo, Waukesha; Richard M. Kulakowski, Richfield, both of WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/349,586

(22) Filed: Jul. 9, 1999

(51) Int. Cl.$^7$ ...................................................... A61B 8/06
(52) U.S. Cl. .............................................................. 600/455
(58) Field of Search ................................... 600/453–456, 600/440–441; 73/861.25

(56) References Cited

U.S. PATENT DOCUMENTS

| | | | |
|---|---|---|---|
| 5,269,308 | * 12/1993 | Hagiwara et al. | 73/861.25 |
| 5,299,174 | * 3/1994 | Forestieri et al. | 367/135 |
| 5,383,464 | * 1/1995 | Shiba | 600/455 |
| 5,443,071 | * 8/1995 | Banjanin et al. | 600/455 |
| 5,544,659 | * 8/1996 | Banjanin | 600/455 |
| 5,910,118 | * 6/1999 | Kanda et al. | 600/455 |
| 6,146,331 | * 11/2000 | Wong | 600/454 |

* cited by examiner

Primary Examiner—Francis J. Jaworski
(74) Attorney, Agent, or Firm—Dennis M. Flaherty; Christian G. Cabou; Peter J. Vogel

(57) ABSTRACT

A method and an apparatus for adaptive wall (high-pass) filtering to remove low-frequency clutter in spectral Doppler I/Q data prior to FFT processing. The I/Q data is passed through a low-pass filter which rejects the flow frequency components above the clutter frequency range. The total power of the low-pass filter output is then computed. A system noise model is used to predict the mean system noise power in the low-pass filter output. The predicted mean noise power provides a noise threshold to gage how much clutter power is present in the current FFT packet. If no significant clutter is present, then wall filter selection logic will automatically select the lowest wall filter cutoff frequency stored in a filter coefficient LUT. If significant clutter power is present in the FFT packet, then the mean and variance of the clutter frequency over the FFT packet are estimated and then input into the filter selection logic, which selects the most suitable filter cutoff for the current clutter signal.

21 Claims, 3 Drawing Sheets

METHOD AND APPARATUS FOR ADAPTIVE WALL FILTERING IN SPECTRAL DOPPLER ULTRASOUND IMAGING

FIELD OF THE INVENTION

This invention relates to ultrasonic diagnostic systems which measure the velocity of blood flow using spectral Doppler techniques. In particular, the invention relates to the continuous display of such information, including maximum and mean blood flow velocities.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. For blood flow measurements, returning ultrasonic waves are compared to a frequency reference to determine the frequency shifts imparted to the returning waves by moving objects including the vessel walls and the red blood cells inside the vessel. These frequency shifts translate into velocities of motion.

In state-of-the-art ultrasonic scanners, the pulsed or continuous wave Doppler waveform is com- puted and displayed in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

In the conventional spectral Doppler mode, an ultrasound transducer array is activated to transmit by a transmit ultrasound burst which is fired repeatedly at a pulse repetition frequency (PRF). The PRF is typically in the kilohertz range. The return radiofrequency (RF) signals are detected by the transducer elements and then formed into a receive beam by a beamformer. For a digital system, the summed RF signal from each firing is demodulated by a demodulator into its in-phase and quadrature (I/Q) components. The I/Q components are integrated (summed) over a specific time interval and then sampled. The summing interval and transmit burst length together define the length of the sample volume as specified by the user. This so-called "sum and dump" operation effectively yields the Doppler signal backscattered from the sample volume. The Doppler signal is passed through a wall filter, which is a high pass filter that rejects any clutter in the signal corresponding to stationary or very slow-moving tissue, including a portion of the vessel wall(s) that might be lying within the sample volume. The filtered output is then fed into a spectrum analyzer, which typically takes the complex Fast Fourier Transform (FFT) over a moving time window of 64 to 256 samples. The data samples within an FFT analysis time window will be referred to hereinafter as an FFT packet. Each FFT power spectrum is compressed and then displayed via a gray map on the monitor as a single spectral line at a particular time point in the Doppler velocity (frequency) versus time spectrogram.

Typically the I and Q components of the Doppler signal are filtered separately by identical wall filters, which can be implemented as either an FIR or IIR filter. For s harp rejection of low-frequency clutter, a narrow transition band in the frequency response of the filter is required. Typically, the wall filter cutoff frequency is manually selected via a front-panel control key. Usually the wall filter cutoff frequency is increased when bright, low-frequency clutter is seen in the spectral image. Each time the wall filter cutoff setting is changed, a corresponding set of filter coefficient values are read out of a lookup table (LUT) and loaded into the wall filters.

The main limitation with the manually selected filter approach in the prior art is that once the cutoff frequency is set, the wall filter does not change even though the clutter frequency and bandwidth may vary with time, due to radial and/or lateral motion of the vessel walls over the cardiac cycle. As a result, the selected filter cutoff is often optimal only for a small portion of the cardiac cycle.

SUMMARY OF THE INVENTION

The present invention is a method and an apparatus for adaptive wall (high-pass) filtering which overcomes the limitation of the prior art manually selected filter approach. In accordance with the preferred embodiment of the invention, the wall filter cutoff frequency is selected automatically, thereby improving ease of use and productivity. A further advantage is that a wall filter cutoff frequency tailored to each new FFT packet can be used.

In accordance with the preferred embodiment of the invention, low-frequency clutter is removed in the Doppler I/Q data prior to FFT processing. The I/Q data is passed through a low-pass filter whose cutoff frequency is set at the highest anticipated clutter frequency (e.g. 40% of PRF) for the current Doppler application. The low-pass filter rejects the flow frequency components above the clutter frequency range. The total power of the low-pass filter output, i.e., the sum of $(I_n^2 + Q_n^2)$ over the FFT (or a fraction of the FFT) packet size M, is then computed.

In accordance with the preferred embodiments, a system noise model is used to predict the mean system noise power in the low-pass filter output. The mean system noise power predicted by the system noise model provides a noise threshold to gage how much clutter power is present in the current FFT packet. If no significant clutter is present, then wall filter selection logic will automatically select the lowest wall filter cutoff frequency in a filter coefficient LUT. If significant clutter power is present in the FFT packet, the algorithm proceeds to compute the mean and variance of the clutter frequency over the FFT packet. The estimated mean and variance of the clutter frequency are then fed into the filter selection logic, which selects the most suitable filter cutoff for the current clutter signal. To avoid having the wall filter cutoff frequency fluctuate too much from one FFT packet to the next, some persistence function may be applied to the prescribed wall filter cutoff frequency. Once the new optimal filter cutoff is selected, the rest of the processing is the same as in conventional Doppler wall filtering.

It should be clear to those skilled in the art that the method of the invention can be implemented in hardware (e.g., a digital signal processing chip) and/or software.

DETAILED DESCRIPTION OF THE PREFERRED EMBODIMENTS

Figure 1:
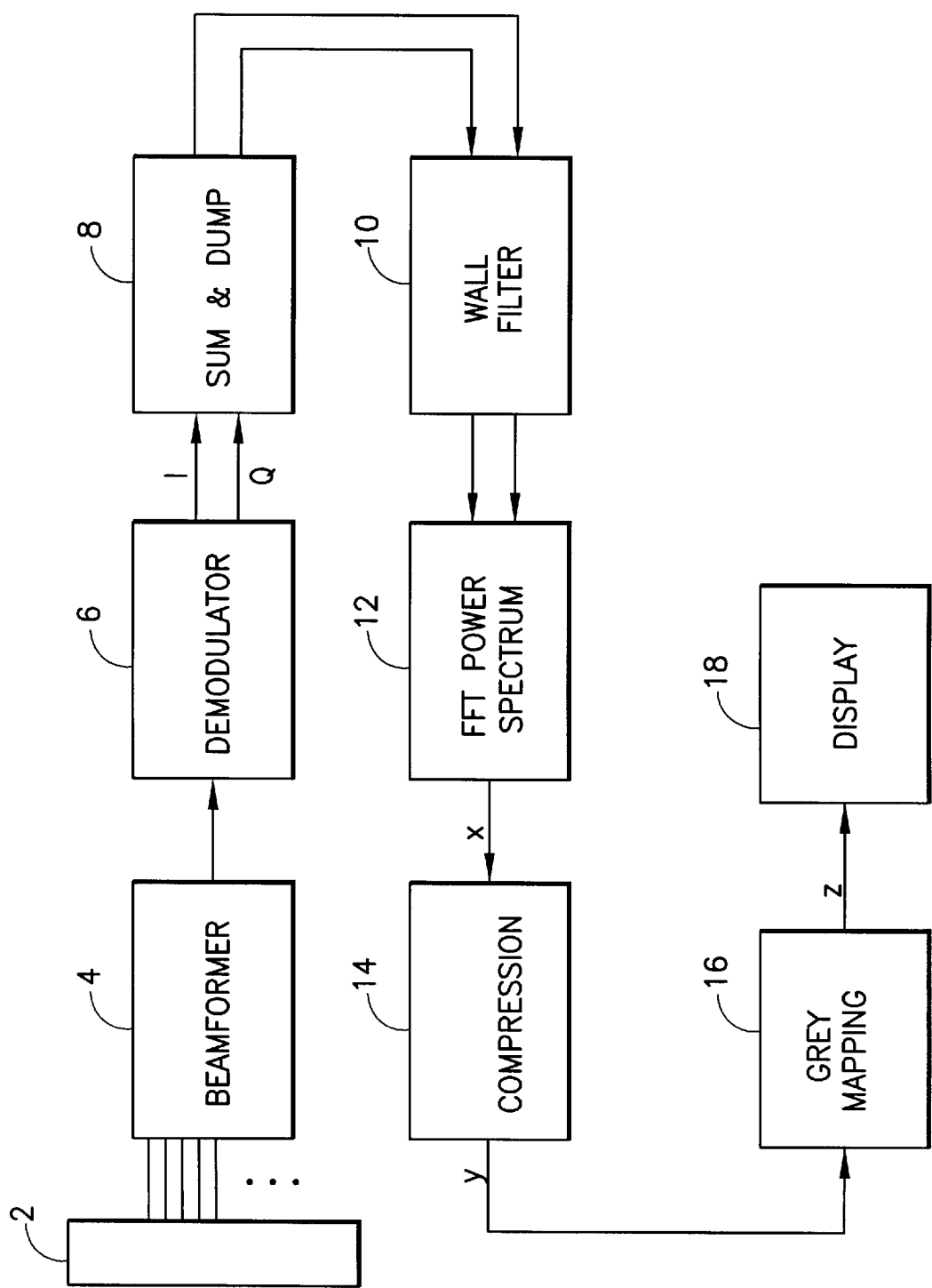
FIG. 1 is a block diagram of the basic signal processing chain in a conventional spectral Doppler imaging system.

A typical digital real-time ultrasonic imaging system having a spectral Doppler imaging mode is generally depicted in FIG. 1. An ultrasound transducer array 2 is activated by a transmitter of a beamformer 4 to transmit ultrasound beams focused at a desired transmit focal position. The transmitter provides a transmit ultrasound burst which is fired repeatedly at a pulse repetition frequency (PRF). The PRF is typically in the kilohertz range. The return RF signals are detected by the transducer elements and then formed into a receive beam by a receiver of beamformer 4. For a digital system, the summed (beamformed) RF signal from each firing is demodulated by demodulator 6 into its in-phase and quadrature (I/Q) components. The I/Q components are integrated (summed) over a specific time interval and then sampled by a "sum and dump" block 8. The summing interval and transmit burst length together define the length of the sample volume as specified by the user. The "sum and dump" operation effectively yields the Doppler signal backscattered from the sample volume. The Doppler signal is passed through a wall filter 10 which rejects any clutter in the signal corresponding to stationary or very slow-moving tissue. The filtered output is then fed into a spectrum analyzer 12, which typically takes the Fast Fourier Transform (FFT) over a moving time window of 64 to 256 samples. Each FFT power spectrum is compressed (block 14) and mapped (block 16) to a gray scale for display on monitor 18 as a single spectral line at a particular time point in the Doppler velocity (frequency) versus time spectrogram.

In one typical spectral Doppler system, the I and Q components of the Doppler signal are filtered separately by identical wall filters, which can be implemented as either an FIR or IIR filter. For sharp rejection of low-frequency clutter, a narrow transition band in the frequency response of the filter is required. IIR filters are generally considered more advantageous because of the large filter length required of an FIR implementation. In conventional spectral Doppler systems, an IIR high-pass filter is usually used, and it is often implemented as a cascade of three or four second-order stages. The input x(n) and the output y(n) of each second-order stage satisfy the following difference equation:

$$y(n) = a_1 y(n-1) + a_2 y(n-2) + b_0 x(n) + b_1 x(n-1) + b_2 x(n-2)$$

Figure 2:
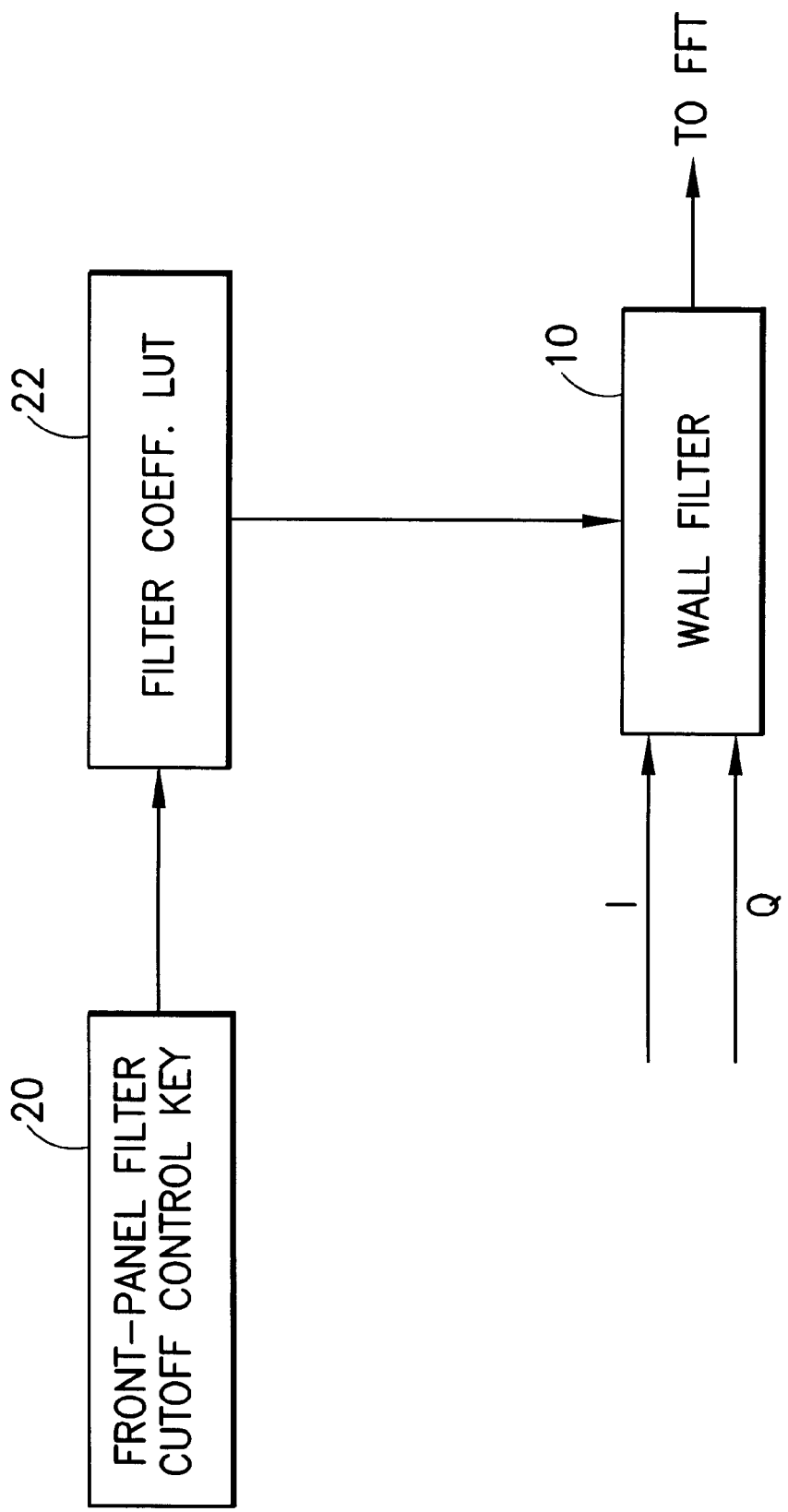
FIG. 2 is a block diagram showing a wall filter and associated components of a spectral Doppler imaging system of the type depicted in FIG. 1.

For a given cutoff frequency, the filter coefficients {$a_1, a_2, b_0, b_1, b_2$} for each second-order stage can be pre-computed using standard filter design formulas and stored in a LUT 22 (see FIG. 2).

Typically, the wall filter cutoff frequency is manually selected via a front-panel control key 20. Usually the wall filter cutoff frequency is increased when bright, low-frequency clutter is seen in the spectral image. Each time the wall filter cutoff setting is changed, a corresponding set of filter coefficient values are read out of the LUT 22 and loaded into the wall filters 10. To minimize transient noise, the y(n−1) and y(n−2) values for each filter stage can be assumed to be zero right after the new filter coefficient set is loaded.

Figure 3:
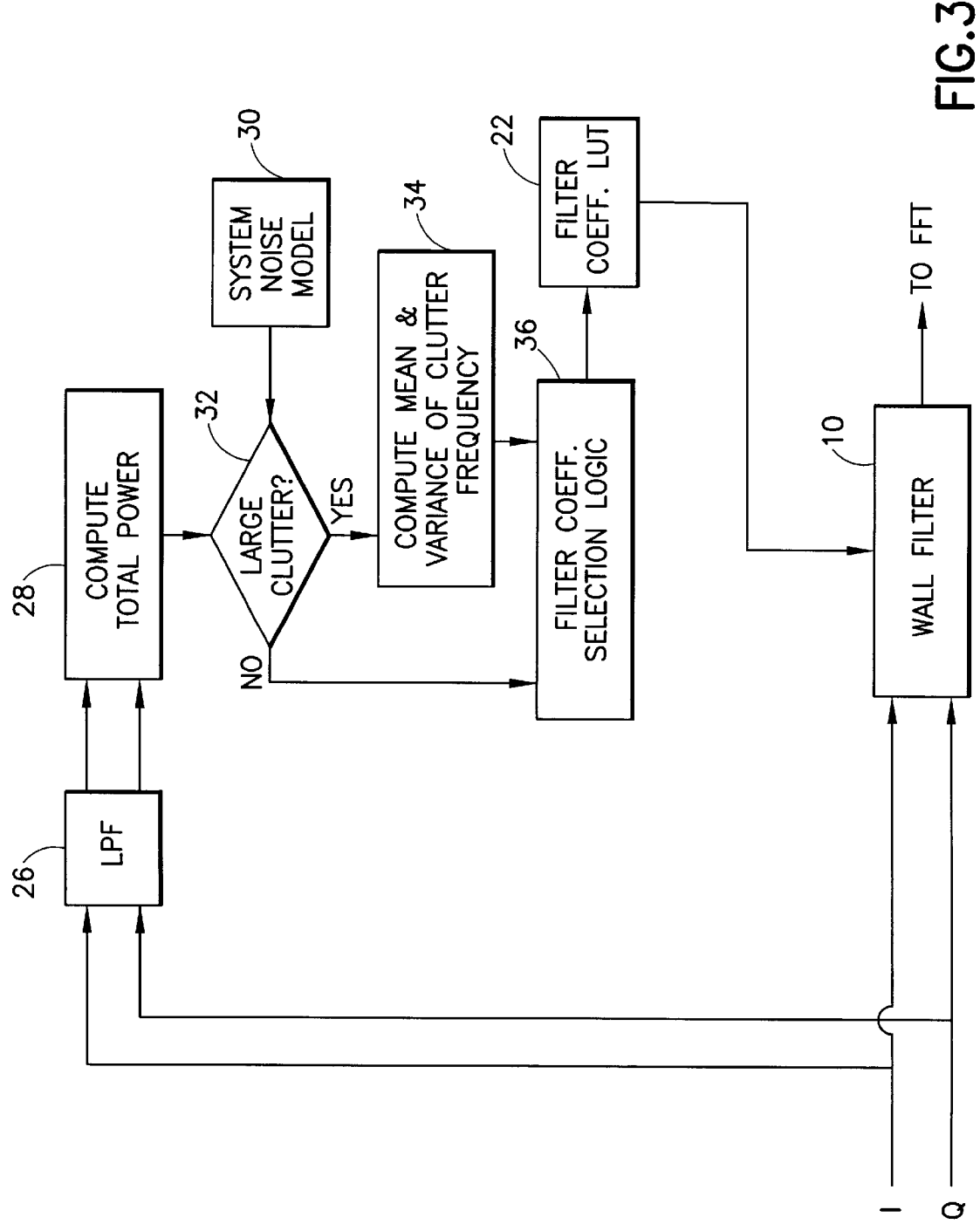
FIG. 3 is a flowchart showing the preferred embodiment of the invention.

The present invention is an improvement over the manual wall filter cutoff frequency technique shown in FIG. 2. In accordance with the preferred embodiment of the invention, low-frequency clutter is removed in the Doppler I/Q data prior to FFT processing. As shown in FIG. 3, the I/Q data is passed through a low-pass filter (LPF) 26 whose cutoff frequency is set at the highest anticipated clutter frequency (e.g. 40% of PRF) for the current Doppler application. The low-pass filter 26 rejects the flow frequency components above the clutter frequency range. The total power of the low-pass filter output, i.e., the sum of $(I_n^2 + Q_n^2)$ over the FFT (or a fraction of the FFT) packet size M, is then computed (step 28).

In accordance with the preferred embodiments, a system noise model 30 is used to predict the mean power of the system noise within the passband of the low pass filter. In the most preferred embodiment, the model assumes an all-digital scanner whose system noise originates primarily from the pre-amplifier in each receive channel in the beamformer. The pre-amp Johnson noise is often specified as a rms voltage per $Hz^{1/2}$ (e.g., 10 $nV/Hz^{1/2}$2) at room temperature. Thus, knowing the equivalent noise bandwidths of all the filters in the Doppler signal path (from the demodulator to the "sum and dump" filter) should enable an absolute rms noise level to be computer as a function of system gain. Any quantization noise due to analog-to-digital conversion in the receiver can also be added in an appropriate manner. Further, knowing the sample volume position and aperture strategy in the spectral Doppler mode, it should be straightforward to compute the total system noise by summing over all active receive channels (including array apodization effects) for a given sample volume position. The mean noise power at the low pass filter output can be computed based on the bandwidth of the low pass filter. It should be apparent to those skilled in the art that similar noise models can be developed for scanners whose Doppler signal paths differ from the basic structure of FIG. 1. Also, while a system noise model is clearly most efficient from an implementation standpoint, a LUT with multiple inputs can be used to perform the same function. Such a LUT can be established either by noise calibration measurements or by simulating the system noise model. In the first alternative, the system is pre-calibrated by trying different combinations of gain settings, recording the resulting noise values and storing those gain settings and corresponding noise values in a LUT. In the second alternative, the noise model values are pre-computed and stored in a LUT.

The model noise power predicted by the system noise model 30 provides a noise threshold to gage how much clutter power is present in the current FFT packet (step 32). For example, if the total power estimate of the filtered FFT packet is not more than, say, 20 dB above the predicted noise power for that packet size, then no significant clutter is present. In this case wall filter selection logic 36 will automatically select the lowest wall filter cutoff frequency in the filter coefficient LUT 22.

If significant clutter power is present in the FFT packet (step 32), the algorithm proceeds to compute the mean and variance of the clutter frequency over the FFT packet (step 34). Different methods for estimating the mean may be used including computing the first moment of the FFT spectrum of the packet, and counting zero-crossings. The preferred method is, however, the standard Kasai estimator which is both accurate and computationally efficient—the same reasons it is also commonly used in color flow imaging systems. For an I/Q packet size of M, the Kasai estimates for the mean and variance of the frequency of the I/Q data are defined by $$E(f) = (1/2\pi) \tan^{-1}(N/D)$$

$$var(f) = 2/(2\pi T)^2 [1 - |R(T)|R(0)]$$

where $$N = \sum_{n=1}^{M-1} (I_n Q_{n+1} - I_{n+1} Q_n)$$

$$D = \sum_{n=1}^{M-1} (I_n I_{n+1} + Q_n Q_{n+1})$$

$$|R(T)| = (N^2 + D^2)^{1/2}$$

$$R(0) = \sum_{n=1}^{M-1} (I_n^2 + Q_n^2 + I_{n+1}^2 + Q_{n+1}^2)/2$$

and T is the sampling period of the I/Q data.

The estimated mean and variance of the clutter frequency are then fed into the filter selection logic 36, which selects the most suitable filter cutoff for the current clutter signal from the LUT 22. For example, the high-pass filter cutoff may be based on the absolute value of the mean frequency, plus, e.g., 3 times the standard deviation. To avoid having the wall filter cutoff frequency fluctuate too much from one FFT packet to the next, some persistence function (incorporated in the selection logic) may be applied to the prescribed wall filter cutoff frequency by, for example, averaging the cutoff frequency estimates over the last several FFT packets. Once the new optimal filter cutoff is selected, the rest of the processing is the same as in conventional Doppler wall filtering (shown in FIG. 2).

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. In particular, it should be clear to those skilled in the art that the method as shown in FIG. 3 can be implemented in hardware (e.g., a digital signal processor) and/or software. Therefore, it is intended that the invention not be limited to the particular embodiment disclosed as the best mode contemplated for carrying out this invention, but that the invention will include all embodiments falling within the scope of the appended claims.

What is claimed is:

1. A system for imaging ultrasound scatterers, comprising:
a transmitter for transmitting a multiplicity of pulses of ultrasound into a sample volume of ultrasound scatterers, said multiplicity of pulses forming a packet;
a receiver for acquiring a multiplicity of sucessive samples of Doppler signals backscattered from said sample volume of ultrasound scatterers;
a display monitor comprising columns of pixels;
a processor for processing said Doppler signals to produce spectral line data representing velocity for continuous display of a succession of spectral lines during Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on said display monitor, said processor comprising:
a demodulator for demodulating said Doppler signal samples into in-phase and quadrature components;
an integrator for integrating the in-phase and quadrature components over a specific time interval;
first and second wall filters for substantially rejecting clutter in the integrated in-phase and quadrature components corresponding to stationary or very slow-moving tissue;
cutoff frequency selection means for selecting the cutoff frequencies of said first and second wall filters as a function of the clutter power of said integrated in-phase and quadrature components; and
a spectrum analyzer for producing spectral power data by Fast Fourier transformation of the wall-filtered in-phase and quadrature components,
wherein said cutoff frequency selection means comprise:
a low pass filter for rejecting flow frequency components in said integrated in-phase and quadrature components which are above a clutter frequency range;
means for computing the total power of the output of said low pass filter;
means for providing an estimate of the mean system noise power in said low pass filter output;
means for comparing the total power of said low pass filter output to the mean system noise power in said low pass filter output; and
filter coefficient selection means for selecting wall filter coefficients which are a function of the results of comparing the total power to the mean system noise power.

2. The system as recited in claim 1, wherein said filter coefficient selection means comprise:
means for computing the mean and variance of the clutter frequency for said low pass filter output; and
memory for storing wall filter coefficients corresponding to different cutoff frequencies; and
selection logic for retrieving wall filter coefficients from said memory as a function of the computed mean and variance of the clutter frequency when said comparing means determine that the total power exceeds the mean system noise power by at least a predetermined amount.

3. The system as recited in claim 2, wherein said means for computing the mean and variance of the clutter frequency employs the standard Kasai estimator.

4. The system as recited in claim 2, wherein said selection logic selects wall filter coefficients corresponding to the lowest cutoff frequency stored in said memory when said comparing means determine that the total power does not exceed the mean system noise power by at least a predetermined amount.

5. The system as recited in claim 1, wherein said cutoff frequency selection means comprise means for selecting the wall filter coefficients in accordance with a persistence function applied over a multiplicity of packets.

6. A method for displaying a Doppler velocity-time waveform envelope, comprising the steps of:
transmitting a multiplicity of pulses of ultrasound into a sample volume of ultrasound scatterers, said multiplicity of pulses forming a packet;
acquiring a multiplicity of successive samples of Doppler signals backscattered from said sample volume of ultrasound scatterers; and
processing said Doppler signals to produce spectral line data representing velocity for continuous display of a succession of spectral lines during Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on a display monitor, said processing step comprising the steps of:

demodulating said Doppler signal samples into in-phase and quadrature components;

integrating the in-phase and quadrature components over a specific time interval;

wall filtering the integrated in-phase and quadrature components to substantially reject clutter corresponding to stationary or very slow-moving tissue;

selecting cutoff frequencies to be used in said wall filtering step as a function of the clutter power of said integrated in-phase and quadrature components; and producing spectral power data by Fast Fourier transformation of the wall-filtered in-phase and quadrature components, wherein said cutoff frequency selecting step comprises the steps of:

low pass filtering said integrated in-phase and quadrature components to substantially reject flow frequency components which are above a clutter frequency range;

computing the total power of the output of said low pass filtering step;

providing an estimate of the mean system noise power in said low pass filtering output;

comparing the total power of said low pass filtering output to the mean system noise power in said low pass filtering output; and selecting wall filter coefficients which are a function of the results of comparing the total power to the mean system noise power.

7. The method as recited in claim 6, wherein said wall filter coefficient selecting step comprises the steps of:

computing the mean and variance of the clutter frequency for said low pass filter output; and pre-storing wall filter coefficients corresponding to different cutoff frequencies; and retrieving wall filter coefficients from said memory as a function of the computed mean and variance of the clutter frequency when the total power exceeds the mean system noise power by at least a predetermined amount.

8. The method as recited in claim 7, wherein said step of computing the mean and variance of the clutter frequency employs the standard Kasai estimator.

9. The method as recited in claim 7, wherein wall filter coefficients corresponding to the lowest pre-stored cutoff frequency are selected when the total power does not exceed the mean system noise power by at least a predetermined amount.

10. The method as recited in claim 7, wherein the wall filter coefficients are selected in accordance with a persistence function applied over a multiplicity of packets.

11. A system comprising:

a transducer array comprising a multiplicity of transducer elements for transmitting wave energy in response to electrical activation and transducing returned wave energy into electrical signals;

a display monitor for displaying spectral Doppler data; and a computer programmed to perform the following steps:

activating transducer elements of said array to transmit a multiplicity of pulses of ultrasound into a sample volume of ultrasound scatterers, said multiplicity of pulses forming a packet;

acquiring a multiplicity of successive samples of Doppler signals backscattered from said sample volume of ultrasound scatterers and detected by said array; and processing said Doppler signals to produce spectral line data representing velocity for continuous display of a succession of spectral lines during Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on said display monitor, said processing step comprising the steps of:

demodulating said Doppler signal samples into in-phase and quadrature components;

integrating the in-phase and quadrature components over a specific time interval;

wall filtering the integrated in-phase and quadrature components to substantially reject clutter corresponding to stationary or very slow-moving tissue;

selecting cutoff frequencies to be used in said wall filtering step as a function of the clutter power of said integrated in-phase and quadrature components; and producing spectral power data by Fast Fourier transformation of the wall-filtered in-phase and quadrature components, wherein said cutoff frequency selecting step comprises the steps of:

low pass filtering said integrated in-phase and quadrature components to substantially reject flow frequency components which are above a clutter frequency range;

computing the total power of the output of said low pass filtering step;

providing an estimate of the mean system noise power in said low pass filtering output;

comparing the total power of said low pass filtering output to the mean system noise power in said low pass filtering output; and selecting wall filter coefficients which are a function of the results of comparing the total power to the mean system noise power.

12. The system as recited in claim 11, wherein said wall filter coefficient selecting step comprises the steps of:

computing the mean and variance of the clutter frequency for said low pass filter output; and pre-storing wall filter coefficients corresponding to different cutoff frequencies; and retrieving wall filter coefficients from said memory as a function of the computed mean and variance of the clutter frequency when the total power exceeds the mean system noise power by at least a predetermined amount.

13. The system as recited in claim 12, wherein said step of computing the mean and variance of the clutter frequency employs the standard Kasai estimator.

14. The system as recited in claim 12, wherein wall filter coefficients corresponding to the lowest pre-stored cutoff frequency are selected when the total power does not exceed the mean system noise power by at least a predetermined amount.

15. A method for displaying Doppler blood flow information, comprising the steps of:
- transmitting a multiplicity of pulses of ultrasound into a sample volume of ultrasound scatterers, said multiplicity of pulses forming a packet;
- acquiring Doppler signals backscattered from said sample volume of ultrasound scatterers;
- low pass filtering the acquired Doppler signals to substantially reject flow frequency components which are above a clutter frequency range;
- computing the total power of the output of said low pass filtering step;
- comparing the total power of said low pass filtering output to an estimated mean system noise power in said low pass filtering output;
- selecting wall filter coefficients which are a function of the results of comparing the total power to the mean system noise power;
- wall filtering the Doppler signals to substantially reject clutter corresponding to stationary or very slow-moving tissue; and
- processing the wall-filtered Doppler signals to produce blood flow data for display.

16. The method as recited in claim 15, wherein said wall filter coefficient selecting step comprises the steps of:
- computing the mean and variance of the clutter frequency for said low pass filter output;
- pre-storing wall filter coefficients corresponding to different cutoff frequencies; and
- retrieving wall filter coefficients from said memory as a function of the computed mean and variance of the clutter frequency when the total power exceeds the mean system noise power by at least a predetermined amount.

17. The method as recited in claim 15, wherein wall filter coefficients corresponding to the lowest pre-stored cutoff frequency are selected when the total power does not exceed the mean system noise power by at least a predetermined amount.

18. An ultrasound imaging system comprising:
- a transmitter for transmitting a multiplicity of pulses of ultrasound into a sample volume of ultrasound scatterers, said multiplicity of pulses forming a packet;
- a receiver for acquiring Doppler signals backscattered from said sample volume of ultrasound scatterers;
- a low pass filter for low pass filtering the acquired Doppler signals to substantially reject flow frequency components which are above a clutter frequency range;
- a wall filter for wall filtering the acquired Doppler signals to substantially reject clutter corresponding to stationary or very slow-moving tissue;
- a display monitor for displaying blood flow data; and
- a computer programmed to perform the following steps:
    - computing the total power of the output of said low pass filter;
    - comparing the total power of said low pass filter output to an estimated mean system noise power in said low pass filter output;
    - selecting filter coefficients for said wall filter which are a function of the results of comparing the total power to the mean system noise power;
    - setting said wall filter in accordance with said selected wall filter coefficients; and
    - processing the wall-filtered Doppler signals to produce blood flow data for display.

19. The system as recited in claim 18, wherein said wall filter coefficient selecting step comprises the steps of:
- computing the mean and variance of the clutter frequency for said low pass filter output;
- retrieving said selected wall filter coefficients from a data table containing a multiplicity of wall filter coefficients corresponding to different cutoff frequencies, wherein said selected wall filter coefficients are a function of the computed mean and variance of the clutter frequency when the total power exceeds the mean system noise power by at least a predetermined amount.

20. The system as recited in claim 18, wherein wall filter coefficients corresponding to the lowest pre-stored cutoff frequency are selected when the total power does not exceed the mean system noise power by at least a predetermined amount.

21. The system as recited in claim 19, wherein wall filter coefficients corresponding to the lowest pre-stored cutoff frequency are selected when the total power does not exceed the mean system noise power by at least a predetermined amount.

* * * * *

UNITED STATES PATENT AND TRADEMARK OFFICE
CERTIFICATE OF CORRECTION

PATENT NO.   : 6,296,612 B1
DATED        : October 2, 2001
INVENTOR(S)  : Larry Y.L. Mo and Richard M. Kulakowski It is certified that error appears in the above-identified patent and that said Letters Patent is hereby corrected as shown below:

Column 1,
Line 25, change "com-puted" to -- computed --.
Line 65, change "s harp" to -- sharp --.

Column 3,
Line 46, change the letter "d" in the equation to the letter "b"

Column 4,
Line 16, delete the boldface "2"
Line 66, insert a slash (/) between the vertical bar (|) and the adjacent letter "R".

Column 10,
Line 39, delete claim 21 and substitute the following claim therefor:
-- 21. The system as recited in claim 11, wherein the wall filter coefficients are selected in accordance with a persistence function applied over a multiplicity of packets. --

Signed and Sealed this

Tenth Day of September, 2002

Attest:

JAMES E. ROGAN
Attesting Officer      Director of the United States Patent and Trademark Office